(12) United States Patent
Brown, Jr. et al.

(10) Patent No.: US 7,452,529 B2
(45) Date of Patent: Nov. 18, 2008

(54) TREATMENT OF MUSCULAR DYSTROPHY WITH CORD BLOOD CELLS

(75) Inventors: Robert H. Brown, Jr., Needham, MA (US); Seth P. Finklestein, Needham, MA (US); Morey Kraus, Jefferson, MA (US)

(73) Assignees: Viacell, Inc., Worcester, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/201,508

(22) Filed: Jul. 23, 2002

(65) Prior Publication Data

US 2003/0118565 A1 Jun. 26, 2003

Related U.S. Application Data

(60) Provisional application No. 60/307,227, filed on Jul. 23, 2001.

(51) Int. Cl.
*A61K 48/00* (2006.01)
*A01N 63/00* (2006.01)
*A61K 35/12* (2006.01)
*A61K 35/14* (2006.01)

(52) U.S. Cl. .............. 424/93.1; 424/93.2; 424/93.21; 424/93.3; 424/520; 424/529

(58) Field of Classification Search ............ 424/93.1, 424/93.2; 435/325, 375, 347, 363, 352
See application file for complete search history.

(56) References Cited

U.S. PATENT DOCUMENTS

| 5,674,750 | A | 10/1997 | Kraus et al. | 435/372 |
| 5,925,567 | A | 7/1999 | Kraus et al. | 435/372 |
| 6,338,942 | B2 | 1/2002 | Kraus et al. | 435/2 |
| 2002/0051762 | A1 | 5/2002 | Raffii et al. | |

FOREIGN PATENT DOCUMENTS

WO    WO 99/37751    7/1999

OTHER PUBLICATIONS

Shon et al, Expert Opion. Biol. Ther. 4(1):1-9, 2004.*
Meagher et al J Hematother. Stem Cell Res. 11(3):445-8, 2002.*
Dell'Agnola et al Blood. 104(13):4311-8, 2004.*
Chao et al, Hematology Am Soc Hematol Educ Program. 354-371, 2004.*
Kong et al, Stem Cells 22:981-993, 2004.*
Bretag, Nature. 450(7173):E23, 2007.*
Kong et al. Human umbilical cord blood cells differentiate into muscle in sjl muscular dystrophy mice. Stem Cells. 22(6):981-93. 2004.*
Beutler, "Gene Therapy," Biol. Blood Marrow Transplant. 5:273-276 (1999).
Dao and Nolta, "Molecular Control of Cell Cycle Progression in Primary Human Hematopoietic Stem Cells: Methods to Increase Levels of Retroviral-Mediated Transduction," Leukemia 13:1473-1480 (1999).
Gussoni et al., "Dystrophin Expression in the *mdx* Mouse Restored by Stem Cell Tranplantation," Nature 401:390-394 (1999).
Koike, "Cryopreservation of Pluripotent and Committed Hemopoietic Progenitor Cells from Human Bone Marrow and Cord Blood," Acta Paediatrica Japonica 25:275-282 (1983).
Lee et al., "Clonal Isolation of Muscle-Derived Cells Capable of Enhancing Muscle Regeneration and Bone Healing," J. Cell Biol. 150:1085-1099 (2000).
Partridge et al., "Conversion of *mdx* Myofibres from Dystrophin-Negative to -Positive by Injection of Normal Myoblasts," Nature 337:176-179 (1989).
Torrente et al., "Intraarterial Injection of Muscle-Derived CD34$^+$ Sca-1$^+$ Stem Cells Restores Dystropin in *mdx* Mice," J. Cell Biol. 152:335-348 (2001).

* cited by examiner

*Primary Examiner*—Sumesh Kaushal
(74) *Attorney, Agent, or Firm*—Clark & Elbing LLP

(57) ABSTRACT

The invention features methods for treating a patient suffering from muscular dystrophy by administration of umbilical cord blood cells, e.g., by IV infusion.

1 Claim, No Drawings

TREATMENT OF MUSCULAR DYSTROPHY WITH CORD BLOOD CELLS

CROSS REFERENCE TO RELATED APPLICATIONS

This application claims the benefit of the filing date of U.S. provisional patent application No. 60/307,227, filed Jul. 23, 2001.

BACKGROUND OF THE INVENTION

Muscular dystrophy represents a family of inherited diseases of the muscles. Some forms affect children (e.g., Duchenne dystrophy) and are lethal within two to three decades. Other forms present in adult life and are more slowly progressive. The genes for several dystrophies have been identified, including Duchenne dystrophy (caused by mutations in the dystrophin gene) and the teenage and adult onset Miyoshi dystrophy or its variant, limb girdle dystrophy 2B or LGMD-2B (caused by mutations in the dysferlin gene). These are "loss of function" mutations that prevent expression of the relevant protein in muscle and thereby cause muscle dysfunction. Mouse models for these mutations exist, either arising spontaneously in nature or generated by inactivation or deletion of the relevant genes. These models are useful for testing therapies that might replace the missing protein in muscle and restore normal muscle function.

Differentiated muscle is composed of multi-nucleated cells or myofibers that have an extraordinary capacity to regenerate. This regenerative capacity exists because muscle possesses primitive muscle precursor cells (muscle stem cells and somewhat more mature cells known as "satellite cells"). These cells lie dormant in muscle and can be activated to make new mononucleated muscle cells (myoblasts) that can adhere to one another and fuse to make new, multi-nucleated myotubes, as well as the more mature muscle cells (that are again multinucleated). Because myofibers arise from the fusion of individual myoblasts, a protein made by one muscle cell is readily accessible to be shared with neighboring muscle cells lacking that protein if the two cells fuse into the same myotube.

Inherent in this concept of myoblast fusion and muscle regeneration is the possibility of cell therapy of muscle diseases. The fusion of a myoblast capable of making a muscular dystrophy protein with muscle cells that lack the protein should correct the deficiency in the resulting myotube. That is, the normal nucleus in the normal myoblasts replaces a gene missing in the dystrophic muscle cells thus achieving gene and protein replacement through cell therapy.

Partridge and colleagues demonstrated more than a decade ago that a mixed population of muscle precursor cells capable of making normal dystrophin protein could fuse into muscle of the mdx mouse that lacks dystrophin and thereby partially replace the missing protein (Partridge et al., Nature 337:176-179, 1989). In the seminal experiments of Partridge, it was not clear precisely what populations of the muscle precursor cells had the capacity to achieve this effect. At least six human trials of myoblast therapy were undertaken in Duchenne and Becker dystrophy patients, using direct intramuscular injections of myoblasts; that none were effective might be interpreted to mean that myoblasts were not sufficiently undifferentiated to participate effectively in muscle cell therapy. This observation stimulated the search for muscle stem cells.

Over the last two years, several muscle biologists have had encouraging initial success in isolating putative muscle stem cells. Moreover, these studies have documented not only that the primitive muscle precursors can fuse into injured muscle to make new muscle, but also that such stem cells or stem-like cells have an extraordinary capacity to circulate in the blood and then to leave the blood to enter sites of focal muscle injury in response to unidentified myotropic factors. Strikingly, in the last three years it has become apparent that cells with features of muscle stem cells may be present in tissues thought previously to be primarily hematogenic, such as the bone marrow. In 1999, Gussoni and colleagues in the Kunkel laboratory reported that a population of primitive cells identified by the presence of a multi-drug resistance transporter as a "side population"(SP) fraction of cells in either the bone marrow or muscle itself could be delivered to dystrophic mdx muscle following tail vein injection (Gussoni et al., Nature 401:390-394, 1999). That these cells included primitive stem cells was strongly suggested by the finding that the same injection could populate muscle tissue with enough normal muscle cells to restore dystrophin expression in up to 10% of myofibers and, at the same, repopulate the bone marrow of previously irradiated recipient mice. Analogous findings were subsequently reported from the laboratories of Huard (Lee et al., J. Cell Biol. 150:1085-1099, 2000) and Bresolin (Torrente et al., J. Cell Biol. 152:335-348, 2001).

At this time, one criterion for defining a cell as a muscle stem cell is the capacity to differentiate to form myoblasts and thereby augment some aspect of muscle regeneration or repair. Typically, the expression of a previously missing protein (like dystrophin) after muscle stem cell infusion provides prima facie evidence that a muscle stem cell is present. To date, no single set of molecules have been identified that uniquely define muscle stem cells. However, an evolving family of surface proteins is being identified that characterizes different stages of differentiation in the muscle cell lineage, as summarized in Table 1.

TABLE 1

Selected Surface Markers Differentially Expressed on Cells in the Muscle Lineage

| Marker | MSC/SP | Satellite cell | MPC/ Myoblast | Myotube |
| --- | --- | --- | --- | --- |
| Sca-1 | + | — | | |
| c-kit | − (?+) | + | | |
| CD34 | + | + | | |
| CD45 (heme lines) | − | − | | |
| Desmin | − | + | | |
| bcl-2 | ? | + | | |
| Flk-1 (VEGFR/kdr) | − (human) | | | |
| M-cadherin | − | + | | |
| Pax-7 | ? +/− | + | | |
| c-met receptor | ? | + | | |
| Multidrug res prot | + | ? | | |
| MyoD | − | − | + | + |
| Myogenin | − | − | + | + |
| MRF4 | − | − | + | + |
| NCAM | − | − | + | ++ |
| CD43 | − | − | − | − |
| CD123 | − | | | |
| CD90 (+ on MP) | + | | | |
| AC133 | −/+ | ? | | |

MSC = muscle stem cell; SP = side population cells; MPC = muscle precursor cells For example, it is likely that a candidate set of stem cells will express the surface antigen CD34 and perhaps other primitive cell surface markers such as AC133, but not lineage markers, such as c-kit or the hematopoietic marker CD45.

Umbilical cord blood cells ("UCB" cells) contain subpopulations with properties of stem cells. Replacement of bone marrow cells can be accomplished via infusion of human UCB cells.

SUMMARY OF THE INVENTION

The invention features a method for treating a patient suffering from muscular dystrophy by administration of human UCB cells. The cells can be administered in any suitable manner, e.g., by injection directly into the muscle or into the blood stream of the patient. Following systemic injection, some UCB cells will migrate to the muscles of the patient and integrate with existing muscle cells where they will provide missing proteins, thus treating the disease.

In an embodiment of the invention, the UCB cells are treated, prior to administration, to increase their number and to render the cells enriched in relatively undifferentiated cells.

The invention also features a cell transplant method for treating a patient suffering from muscular dystrophy that also reduces the rejection of the administered cells by the immune system of the patient treated. The method includes providing a preparation of cord blood cells, reconstituting the immune system of the patient using cells of the preparation, and administering cells of the preparation to treat the patient's muscular dystrophy. In an embodiment of the cell transplant method, the method further includes expanding the cells of the preparation in vitro and repeatedly administering the expanded cells of the preparation to the patient to treat the patient's muscular dystrophy.

The invention provides several advantages. For example, it provides methods for treating a patient diagnosed with or suffering from muscular dystrophy by administering UCB cells to the patient. The invention relies on the use of umbilical cord blood which contains a rich source of pluripotent stem cells, the precursors of two or more cell types of an organism. Bone marrow from donors has traditionally been used as a source of stem cells for restoration of diseased bone marrow, but researchers have demonstrated that umbilical cord blood provides an excellent alternative source of pluripotent cells that can be used to restore cells of many different tissues. The invention also features a method of treating a patient diagnosed with or suffering from muscular dystrophy in which the patient is administered UCB cells, but, in an effort to overcome a rejection of the cells, the patient's immune system is also reconstituted using the UCB cells (which can be provided by the patient or by a donor).

In addition, cord blood stem cells are unique in that they have been found to be successful in transplant cases when the blood type is only a near match as opposed to stem cells found in bone marrow which require an exact match from donor to recipient. There is also a greater occurrence of graft vs. host disease in bone marrow transplants than there is in cord blood stem cell transplants.

DEFINITIONS

By "umbilical cord blood cells, cord blood cells, or placental blood cells" we mean the blood that remains in the umbilical cord and placenta following birth. Like bone marrow, cord blood has been found to be a rich source of stem cells.

By "stem cell" or "pluripotent stem cell," which can be used interchangeably, is meant a cell having the ability to give rise to two or more cell types of an organism.

DETAILED DESCRIPTION

Mouse Experiments

Human UCB cells are obtained from the umbilical cord of newly born infants immediately following the resection of the cord from the infant. The cells (10,000-1,000,000 cells per mouse) are suspended in standard pharmaceutical buffer or sterile saline and placed in a syringe.

The initial mouse model to be used is a mutant mouse (the sjl mouse) lacking functional dysferlin; these mice are a naturally occurring model of Miyoshi muscular dystrophy/LGMD2B. These mice, described in (Lee et al., J. Cell Biol. 150:1085-1099, 2000), are available in the laboratory of Robert H. Brown, Jr., of the Massachusetts General Hospital, Boston, Mass.

The UCB cells are injected into the bloodstream of the mice via retro-ocular or tail vein injection. After 80 to 100 days, the mice are sacrificed to determine whether the UCB infusions have enhanced muscle regeneration and dysferlin expression. Several endpoints are used to monitor these outcomes including: (a) immunostaining for markers of nuclei of human origin, to define the persistence of the UCB in the muscle tissue; (b) detection in the UCB cells of markers that confirm that the cells have differentiated into muscle; and (c) detection of dysferlin, which the host sjl mice lack. Another method to track the fate of the injected UCB cells is to label them with one or more fluorescent DNA-binding dyes prior to infusion; the presence of those dyes in the nucleus of muscle cells 80 to 100 days after infusion strongly indicates the cells are derived from UCB cells. It is also possible to pre-label the donor cells with 5-bromo-2'-deoxy-uridine (BrDU) or with a nuclear dye such as one of the Hoechst dyes. Functional studies will also be performed to quantitate motor function in the animals.

One or more methods of immunosuppression will be employed to allow the host mice to accept the incoming UCB cells. This can be achieved pharmacologically with, for example, cyclopsorin A, or other immunosuppressant drugs. An alternate approach is to use near-lethal irradiation. Still a third approach to over-coming the transplantation barriers posed by the immune system is to use mice that are immunologically defective (e.g. nu/nu or Rag-null mice).

These initial experiments will employ whole populations of UCB cells. Subsequent experiments will employ subsets of UCB cells, enriched for various categories of stem cells or muscle precursor cells. Among the methods of enrichment are those described in Kraus, U.S. Pat. Nos. 5,925,567 and 5,674,750, hereby incorporated by reference.

Human Therapy

Systemic Infusions

The method of the invention can be used to treat any human patients, whether children or adults, who suffer from one of the forms of muscular dystrophy.

UCB cells are prepared as described above, with the cell number increased proportionally. Preferably, the cells are typed using the standard six transplantation markers; preferably, the match is at least 4/6; most preferably, there is a 6/6 match. In instances in which the match is less than 4/6, however, the procedure may still be viable, with acceptably mild rejection due to the naivete of the relatively undifferentiated UCB cells. What rejection does occur is controlled using the standard methods described above, e.g., the administration of cyclosporin A.

If the UCB cells have not been expanded and selected as described above, the cells can be used in the form in which they are stored. In instances where the number of cells in a single stored sample is insufficient, several such samples can be combined to provide the required number of cells. Further, as is discussed above in connection with the mouse experiments, rather than using the whole UCB cell population, sub-populations can be used that are enriched in muscle stem cells or other precursor cells.

It is anticipated that human therapy is likely to require multiple infusions of either the whole UCB cell preparation or various enriched and expanded sub-populations of the cells. Several infusions of cells can be administered over time, e.g., one on day one, a second on day five, and a third on day ten. After the initial ten day period, there can be a period of time, e.g., two weeks without cell administration, after which time the ten-day administration protocol can be repeated.

Whether administered as a single infusion therapy or multiple infusion therapies, it is likely that the recipient will require immunosuppression. The protocols followed for this will follow the precedents now used in human transplantation for bone marrow replacement (i.e., cell transplantation), with such agents as cyclosporin A and FK506.

Intramuscular Injections

Another possible administration route for UCB cells, or expanded sub-populations of UCB cells, is via direct injection into muscle. It is well established that under certain circumstances direct intramuscular injection of muscle precursor cells can lead to the incorporation of the donor cells into the host, with partial replacement of a missing protein (e.g., dystrophin in the mdx mice). It is also well established that direct myoblast injections into humans with muscular dystrophy is safe, although such myoblasts have not been incorporated significantly into the host muscles. Accordingly, it is believed that sub-populations of UCB cells that are more primitive than myoblasts will fuse into host muscle and thereby permit protein replacement and muscle regeneration. This is inherently less efficient than IV injection for widespread distribution of the injected cells, and thus would almost certainly require multiple injections into multiple muscles.

Immune Reconstitution and Serial Injections by UCB Cells

As is outlined above, maintenance of the donor UCB cells within the host muscle is likely to require chronic use of one or more immunosuppressant regimens. This is analogous to the long-term use of immunosuppressant drugs or other therapy in patients who undergo whole organ or cell transplantation.

The method of using UCB cells proposed herein may circumvent the chronic use of immunosuppressants. The concept has two elements. First, if the recipient undergoes ablation of bone marrow prior to the UCB infusion, it may be possible to replace the recipient's marrow with the UCB cells. It may be possible to provide the recipient's own UCB cells. This may overcome the need for immunosuppression. If the recipient's own UCB cells are not available, donor UCB cells may be used. The donor UCB cells that reconstitute the ablated marrow will effectively tolerize to the host and thereby survive after a period of weeks or months without on-going immunosuppression. In effect, such a recipient is chimeric, with a reconstituted immune system predominantly of donor origin co-existing with host tissues. The second key element in this reconstitution concept is that subsets of UCB cells have an extraordinary capacity to proliferate. We will determine whether the UCB cells used to supply the proteins lacking in the muscles of the dystrophy patients can be used, in parallel, to generate, in vitro, large populations of muscle precursor cells. If indeed the donor UCB cells tolerize to the host and render the host chimeric, then subsequent infusions of the muscle precursor cells derived from the same UCB cells should be immunologically acceptable to the host, even when given in multiple serial infusions. That is, immune reconstitution by UCB cells may permit subsequent serial infusions of muscle precursor cells derived initially from the same UCB donor. In this protocol, once chimerism is established, the subsequent muscle cell infusions should not require immunosuppression of the host.

Collection and Expansion of Umbilical Cord Blood Cells

The UCB cells can be collected by methods known in the art, see for example Koike et al., Acta Paediatrica Japonica 25:275-282, 1983, and expanded by methods described in, for example, U.S. Pat. No. 5,674,750, U.S. Pat. No. 5,925,567, and U.S. Pat. No. 6,338,942. In general precursor cells that can be obtained from umbilical cord blood can be used in accordance with the present invention. The stem cells can be expanded under cell growth conditions, i.e., conditions that promote proliferation ("mitotic activity") of the cells.

Gene Therapy

Gene therapy can also be used to modify the UCB cells to provide one or more missing protein(s) that are the basis for the muscular dystrophy. It is envisioned that UCB cells, which contain subpopulations of stem cells and can be used to replace bone marrow cells, can be modified with a corrected gene product and administered to the patient using one or more of the methods described above. Delivery of the altered UCB cells would then treat the patient's muscular dystrophy.

An exemplary therapeutic gene therapy regimen may include the steps of obtaining a source of UCB cells from a subject or donor, UCB cell enrichment in vitro, UCB cell expansion by methods known in the art, transduction of UCB cells with a vector containing a gene of interest, and reintroduction into the subject. Transduction of the UCB cells by gene therapy techniques can be during or after expansion.

Several methods are known in the art for altering cells for use in gene therapy. These methods include cell transduction (see, e.g., Buetler, Biol. Blood Marrow Transplant 5:273-276, 1999; Dao, Leukemia 13:1473-1480, 1999; and see generally Morgan et al., Ann. Rev. Biochem. 62:191-217, 1993; Culver et al., Trends Genet.10:174-178, 1994; and U.S. Pat. No. 5,399,346 (French et al.)); the use of viral vectors; and the use of non-viral vectors, for example, naked DNA delivered via liposomes, receptor-mediated delivery, calcium phosphate transfection, lipofection, electroporation, particle bombardment (gene gun), microinjection, cell fusion, chromosome-mediated gene transfer, microcell-mediated gene transfer, spheroplast fusion, and pressure-mediated gene delivery. The technique should provide for the stable transfer of the gene to the cell, so that the gene is expressible by the cell and preferably heritable and expressible by its cell progeny.

For general reviews of the methods of gene therapy, see Goldspiel et al., Clinical Pharmacy 12:488-505, 1993; Wu and Wu, Biotherapy 3:87-95, 1991; Tolstoshev, Ann. Rev. Pharmacol. Toxicol. 32:573-596, 1993; Mulligan, Science 260:926-932, 1993; and Morgan and Anderson, Ann. Rev. Biochem. 62:191-217, 1993. Methods commonly known in the art of recombinant DNA technology that can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

What is claimed is:

1. A method for treating a patient suffering from Duchenne's muscular dystrophy, said method comprising the step of administering to said patient's blood stream human umbilical cord blood (UCB) cells, wherein the administration of said UCB cells results in engraftment of UCB-derived muscle cells that express dystrophin, thereby treating said patient by regenerating muscle mass.

* * * * *